United States Patent
Hyatt

[11] Patent Number: 5,999,699
[45] Date of Patent: *Dec. 7, 1999

[54] THERMAL RETENTION DEVICE WITH OUTER COVERING RECEIVING A WARMER AND FOOD TO BE HEATED

[75] Inventor: Gary F. Hyatt, Randleman, N.C.

[73] Assignee: Vesture Corporation, Asheboro, N.C.

[*] Notice: This patent is subject to a terminal disclaimer.

[21] Appl. No.: 09/030,348

[22] Filed: Feb. 25, 1998

Related U.S. Application Data

[63] Continuation of application No. 08/901,826, Jul. 28, 1997, Pat. No. 5,750,962, which is a continuation of application No. 08/394,491, Feb. 27, 1995, abandoned.

[51] Int. Cl.⁶ ...................................................... H05B 3/34
[52] U.S. Cl. ........................... 392/339; 219/528; 219/387; 219/530; 392/346; 126/263.01
[58] Field of Search ..................................... 392/337, 346; 219/528–530, 540, 549, 386–387, 618, 730; 126/263.01, 263.03, 204, 400

[56] References Cited

U.S. PATENT DOCUMENTS

| | | |
|---|---|---|
| D. 287,921 | 1/1987 | Skamser . |
| 1,439,094 | 12/1922 | Gingras . |
| 1,558,278 | 10/1925 | Phillips . |
| 2,114,396 | 4/1938 | McFarlan et al. ........................ 392/339 |
| 2,298,299 | 10/1942 | Joy et al. . |
| 2,479,268 | 8/1949 | Sarria . |
| 2,584,302 | 2/1952 | Stein . |
| 2,980,881 | 4/1961 | McKee . |
| 3,017,493 | 1/1962 | Cooke . |
| 3,079,486 | 2/1963 | Winchell . |
| 3,084,241 | 4/1963 | Carrona . |
| 3,202,801 | 8/1965 | Saluri . |
| 3,273,634 | 9/1966 | Snelling . |
| 3,292,628 | 12/1966 | Maxwell et al. . |
| 3,549,861 | 12/1970 | Trachtenberg et al. .................. 219/387 |
| 3,596,059 | 7/1971 | Hager, Jr. . |
| 3,665,939 | 5/1972 | Laing . |
| 3,721,803 | 3/1973 | DiStefano ................................ 219/387 |
| 3,780,262 | 12/1973 | Rudd . |
| 3,805,018 | 4/1974 | Luong et al. . |
| 4,035,606 | 7/1977 | Browder . |
| 4,134,004 | 1/1979 | Anderson et al. ........................ 219/387 |
| 4,147,921 | 4/1979 | Walter et al. . |
| 4,198,559 | 4/1980 | Walter et al. . |
| 4,199,021 | 4/1980 | Thoma . |
| 4,201,218 | 5/1980 | Feldman et al. . |
| 4,335,725 | 6/1982 | Geldmacher . |
| 4,528,439 | 7/1985 | Marney, Jr. et al. . |
| 4,561,441 | 12/1985 | Kolodziej . |
| 4,578,814 | 3/1986 | Skamser . |
| 4,672,178 | 6/1987 | Wada et al. . |
| 4,702,235 | 10/1987 | Hong . |
| 4,743,726 | 5/1988 | Hughes et al. . |
| 4,777,346 | 10/1988 | Swanton, Jr. . |
| 4,802,233 | 1/1989 | Skamser . |

(List continued on next page.)

FOREIGN PATENT DOCUMENTS

| | | |
|---|---|---|
| 0 001 151 A3 | 3/1979 | European Pat. Off. . |
| 130478 | 1/1985 | European Pat. Off. . |
| 57-96978 | 6/1982 | Japan . |
| 2054348 | 2/1981 | United Kingdom . |
| 2 160 965 | 1/1986 | United Kingdom . |
| 2195015 | 3/1988 | United Kingdom . |
| 2272969 | 6/1994 | United Kingdom . |
| 8706803 | 11/1987 | WIPO . |

OTHER PUBLICATIONS

Ingrid Inc. advertisements for Thermal Bags (6 pages) (Date Unknown).

*Primary Examiner*—John A. Jeffery
*Attorney, Agent, or Firm*—Merchant & Gould P.C.

[57] ABSTRACT

A heat retention device in the form of a heating pad includes an electrically resistive coil contained within a volume. The coil terminates at an electric coupler which is external of the volume. A phase change material is contained within the volume in thermal conductivity with the resistive element.

12 Claims, 3 Drawing Sheets

U.S. PATENT DOCUMENTS

| | | |
|---|---|---|
| 4,806,736 | 2/1989 | Schirico ................................. 219/386 |
| 4,816,646 | 3/1989 | Solomon et al. . |
| 4,817,704 | 4/1989 | Yamashita . |
| 4,868,898 | 9/1989 | Seto . |
| 4,894,931 | 1/1990 | Senee et al. . |
| 4,904,846 | 2/1990 | Oscadal . |
| 4,916,290 | 4/1990 | Hawkins ................................ 219/385 |
| 4,920,964 | 5/1990 | Francis, Jr. . |
| 4,933,534 | 6/1990 | Cunningham et al. ................ 219/387 |
| 4,979,923 | 12/1990 | Tanaka . |
| 4,983,798 | 1/1991 | Eckler et al. . |
| 5,009,228 | 4/1991 | Clark . |
| 5,050,595 | 9/1991 | Krafft . |
| 5,052,369 | 10/1991 | Johnson . |
| 5,062,414 | 11/1991 | Grim . |
| 5,128,522 | 7/1992 | Marx et al. . |
| 5,150,707 | 9/1992 | Anderson . |
| 5,151,578 | 9/1992 | Phillips ................................... 219/549 |
| 5,211,949 | 5/1993 | Salyer . |
| 5,300,105 | 4/1994 | Owens . |
| 5,314,005 | 5/1994 | Dobry . |
| 5,329,096 | 7/1994 | Suematsu . |
| 5,336,255 | 8/1994 | Kanare et al. . |
| 5,339,541 | 8/1994 | Owens . |
| 5,357,693 | 10/1994 | Owens . |
| 5,405,671 | 4/1995 | Kamin et al. . |
| 5,424,519 | 6/1995 | Salee . |
| 5,750,962 | 5/1998 | Hyatt ...................................... 219/528 |
| 5,880,435 | 3/1999 | Bostic ..................................... 219/387 |
| 5,884,006 | 3/1999 | Frohlich et al. ....................... 392/339 |
| 5,892,202 | 4/1999 | Baldwin et al. ....................... 219/387 |

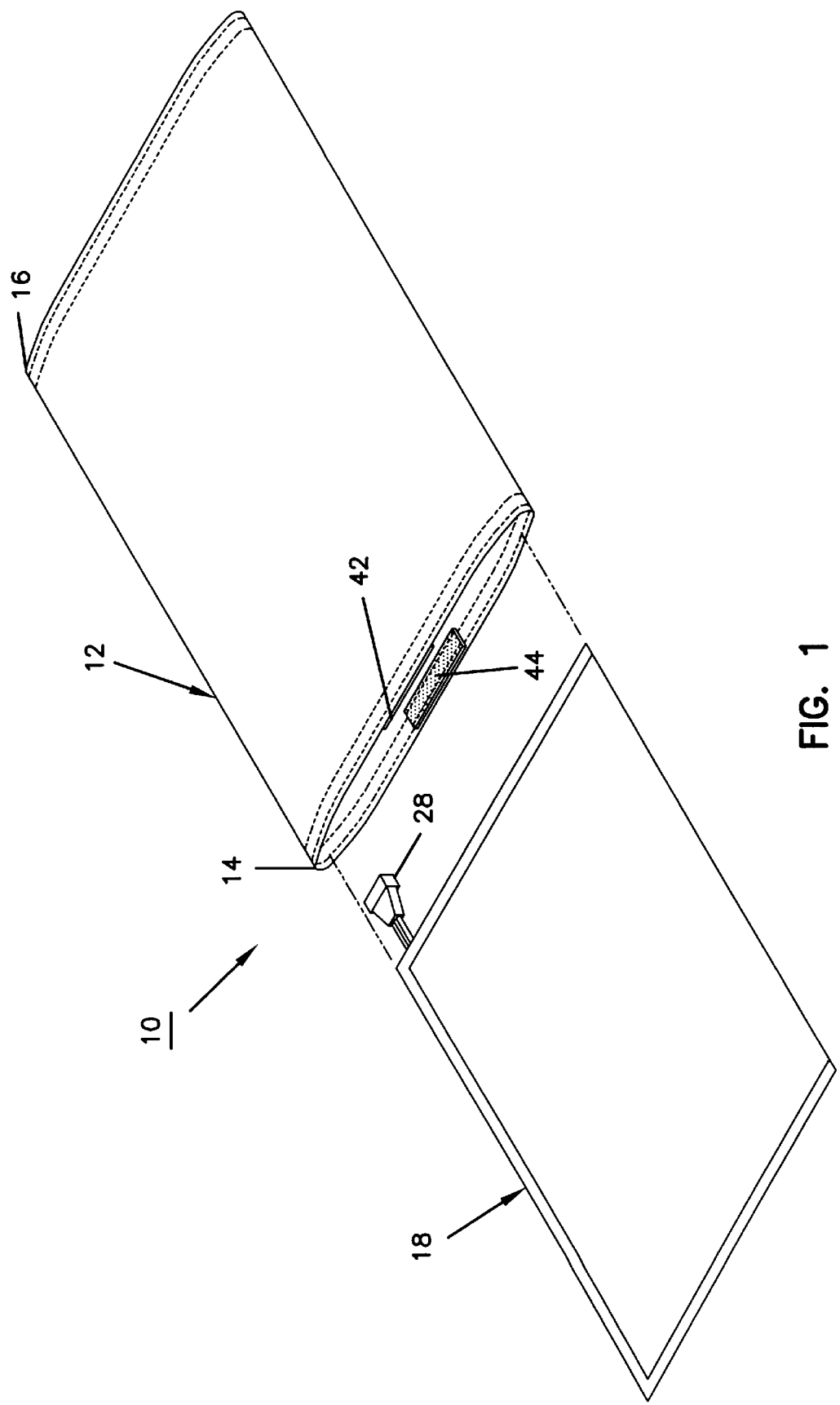

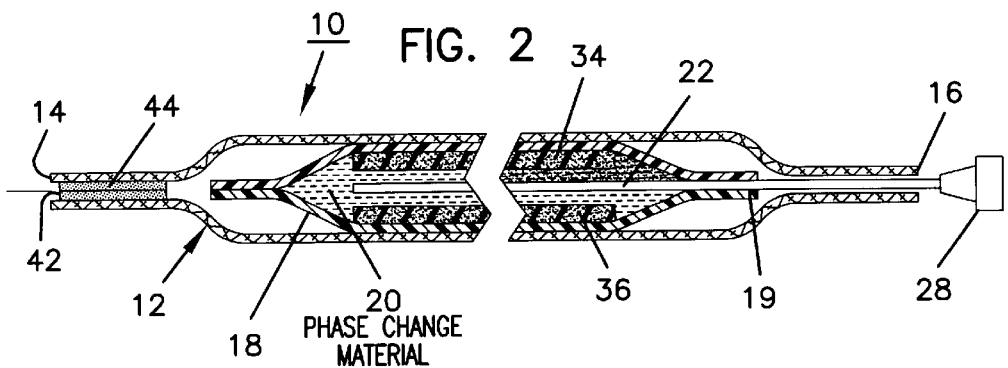
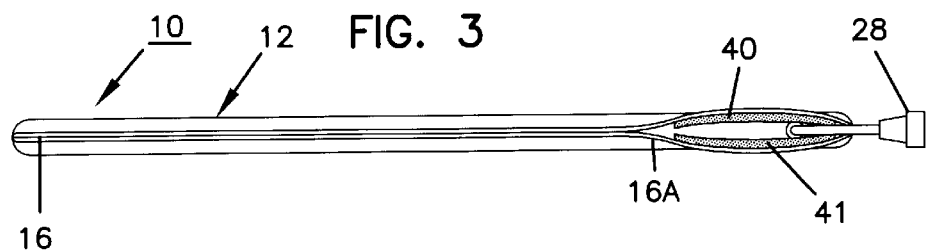
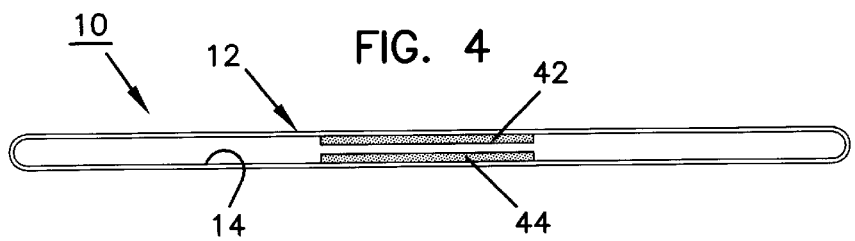
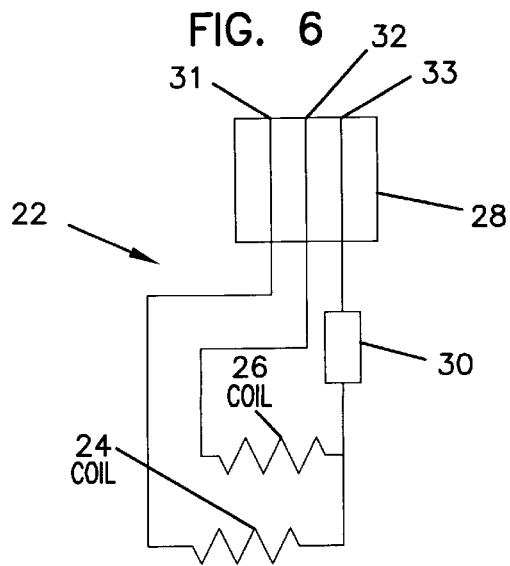

5,999,699

THERMAL RETENTION DEVICE WITH OUTER COVERING RECEIVING A WARMER AND FOOD TO BE HEATED

This application is a Continuation of application Ser. No. 08/901,826, filed Jul. 28, 1997 now U.S. Pat. No. 5,750,962. Application Ser. No. 08/901,826 is a continuation of application Ser. No. 08/394,491, filed Feb. 27, 1995. Both applications are incorporated herein by reference.

BACKGROUND OF THE INVENTION

1. Field of the Invention

This invention pertains to thermal retention devices for storing thermal energy and releasing the thermal energy over time. More particularly, this invention pertains to a thermal retention device which utilizes a phase change material as a medium for storing and releasing thermal energy.

2. Description of the Prior Art

The prior art includes so-called phase change materials. A phase change material is a material which includes a substance which changes phase (for example, from solid state to liquid state or from a liquid state to a gaseous state) upon the application of thermal energy to the material. The process of changing phase results in energy (referred to as latent heat) being stored in the material. When the phase change reverses, the latent heat is released.

Phase change materials can be provided with a wide variety of phase change temperatures (i.e., the temperature at which the phase change material changes phase). An example of a phase change material is described more fully in U.S. Pat. No. 5,211,949 which describes a hydrocarbon dispersed within a finely divided silica. The phase change material stays in a powder form above and below the melting point of the hydrocarbon. The hydrocarbon melting point can be selected to be any one of a number of different temperatures. The phase change material results in an effective storing of thermal energy with energy being released at about the melting point of the hydrocarbon.

Numerous devices containing phase change materials are known in the prior art. For example, seat cushions are formed which will include a foam pad impregnated with a phase change material. The seat cushion is contained within an envelope of plastic such as vinyl or the like. The entire cushion may be placed in a source of thermal energy (for example, a conventional microwave oven). Energy is applied to the phase change material and the cushion will retain an elevated temperature for a substantial period of time (commonly one to four hours). U.S. Pat. No. 5,300,105 discloses a therapeutic pad containing a phase change material.

While prior art microwave thermal retention devices are acceptable for many uses, there are certain applications where such devices have limitations. For example, the user of such a device must have access to a source of the energy. In the case of a microwave thermal retention device, the user must have access to a microwave oven to supply the necessary energy to cause the phase change material to change phase and store the energy. For many users, access to a microwave oven is not practical. Also, for many users, there may be a substantial period of time between which the energy is applied to the phase change material and the device is to be used. An example of such an inconvenience is where a phase change device is to be used as a cushion for either outdoor activity or for stadium use at sporting events and the like. In such cases, there may be a substantial period of time between the application of energy to the phase change material and the use of the device.

SUMMARY OF THE INVENTION

According to a preferred embodiment of the present invention, a thermal retention device is disclosed which includes an envelope for defining an enclosed volume. An electrically resistive element is disposed within the envelope and terminates at an electric coupler which is adapted for coupling to an external source of electric power. A phase change material is contained within the envelope in thermal conductivity with the resistive-element.

BRIEF DESCRIPTION OF THE DRAWINGS

FIG. 1 is a perspective view of a heating pad incorporating the invention of the present invention shown with an internal envelop removed from a cloth cover;

FIG. 2 is a cross-sectional view of the heating pad of FIG. 1;

FIG. 3 is an end view of a first end of the heating pad of FIG. 1 taken along lines 3—3 of FIG. 1;

FIG. 4 is an opposite end view of the heating pad of FIG. 1;

FIG. 6 is a schematic representation of the heating coil shown in FIG. 5;

DESCRIPTION OF A PREFERRED EMBODIMENT

With initial reference to FIG. 1, a heating pad 10 is shown incorporating the teachings of the present invention. It will be appreciated while the present invention is disclosed with reference to a heating pad such as a cushion or the like, that the teachings of the present invention are readily adapted to a wide variety of products and uses.

Figure 5:
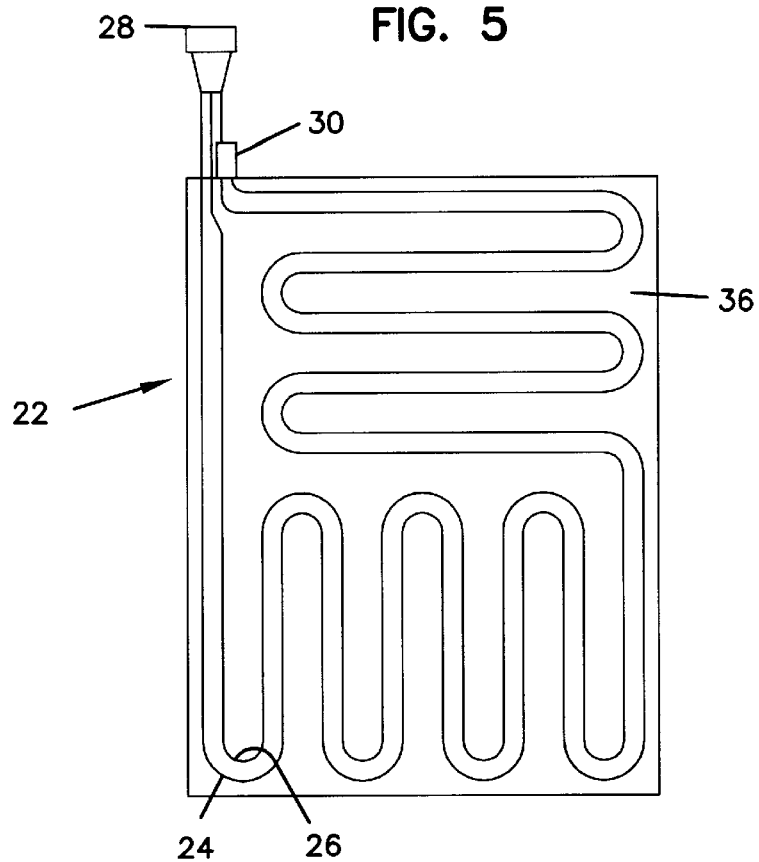
FIG. 5 is a plan view of a resistive heating element of the heating pad of FIG. 1 shown in plan view.

The heating pad 10 is substantially rectangular in shape. The pad 10 includes an outer cloth covering 12 which is open at its opposite ends 14, 16. Contained within cloth covering 12 is a sealed vinyl or plastic envelope 18. Envelope 18 is completely sealed to define an internal volume. Contained within the volume is an electric resistive element (FIGS. 2, 5 and 6) in the form of a plurality of wire coils 22.

The resistive element 22 in a preferred embodiment includes a first resistive coil 24 and a second resistive coil 26. The coils 24, 26 terminate at a coupling 28 which includes three female connectors 31, 32 and 33. Connector 31 and connector 33 are electrically connected to opposite ends of coil 24. Connector 32 and connector 33 are connected to opposite end of coil 26 as best shown schematically in FIG. 6. Each of coils 26, 24 are connected to connector 33 through a thermal switch 30 which will be more fully described. Also, as will be described, coil 24 is intended for use in an alternating current circuit and coil 26 is intended for use in a direct current circuit. A coupling 28 for terminating the coils 24, 26 is shown and described in U.S. Pat. No. 2,980,881.

The coils 24, 26 are disposed sandwiched between two layers of open cell foam material 34, 36 (FIG. 2). The foam material 34, 36 is also contained within the volume of envelope 18. The coupling 28 is exterior to the envelope 18 passing through and sealed at the envelope 18 at location 19. Also contained within envelope 18 is a microwave receptive phase change material 20.

In the specific embodiment shown, a preferred phase change material 20 is sold under the name "Michemlube 270R" available through Mechelman, Inc., 9080 Shell Road, Cincinnati, Ohio, Order No. A56141. Such a phase change material is selected to have a phase change temperature of about 140° F. and is a parfain based emulsion.

With the coils 24, 26, foam 34, 36 and phase change material 20 contained within envelope 18, the envelope 18 (which is flexible plastic) has a vacuum applied to its interior and the peripheral edges of the envelope 18 are completely sealed while the vacuum is applied. Commonly assigned U.S. Pat. No. 5,300,105 teaches sealing a phase change liquid and a foam pad within a flexible plastic envelope.

With the envelope 18 and its contents constructed as thus described, the envelope 18 is contained within the cloth cover 12. The ends 16, 14 of cloth cover 12 are initially open. As best shown in FIG. 3, end 16 is stitched shut substantially along its length but is open at a corner 16A. The opening of corner 16A is sized to freely pass coupling 28. Opposing surfaces of the edge 16 at opening end 16A are provided with hook-and-loop fasteners 40, 41 (such as well-known Velcro™ fasteners) to permit the end 16A to be closed as snugly as possible around the cord extending from coupling 28. The opposite end 14 is also provided with hook-and-loop fasteners 42, 44 to permit end 14 to be closed.

Figure 7:
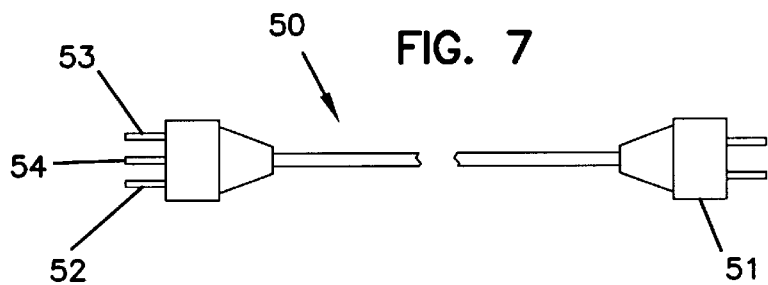
FIG. 7 is a plan view of an alternating current power cord for energizing the pad of FIG. 1.
Figure 8:
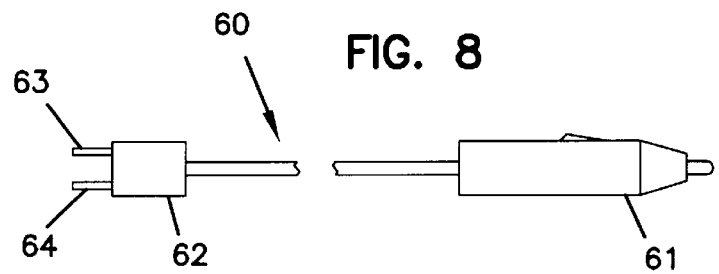
FIG. 8 is a plan view of a direct current power cord for energizing the pad of FIG. 1.

To energize the resistive elements 24, 26, power cords 50, 60 are provided as shown in FIGS. 7 and 8. Power cord 50 is an alternating current power cord having a standard male plug end 51 which may be plugged in any conventional wall outlet and terminating at a coupling 52 having male connectors 53, 54, 55 disposed to be received and mate with the female connectors 31, 32, 33 of coupling 28. Only connectors 53, 55 are connected to plug 51 (connector 54 is not connected to a power source or ground). Power cord 60 is a direct current power cord having a plug end 61 which is a conventional plug to be received within a conventional cigarette lighter in automobiles. Plug 60 terminates at a coupling end 62 provided with male connectors 63, 64 disposed to engage and mate with female connectors 32, 33 of coupling 28. Plug 61 is adapted for a 12 volt DC battery and plug 51 is adapted for insertion into a standard 120 volt AC outlet.

In a preferred use as a cushion or the like, it is desirable to provide energy to the coils 24, 26 at a sufficient rate to enable as rapid heating as possible of the pad 10. In the preferred embodiment, direct current coil 26 is selected to have a resistive value of about 0.08 ohms per foot and with a length of about 18 feet. Resistive coil 24 is selected to have a resistance of 11 ohms per foot and length of about 13 foot. If faster heating is desired, higher resistive valves can be used.

As previously noted, both of resistive elements 24, 26 terminate at neutral connector 33 across a thermal switch 30. Thermal switches are well known in the art and preferably, thermal switch 30 is selected to be a normally closed switch which opens in response to a sensed temperature of 150° F. (i.e., 100 above the phase change temperature of the preferred phase change material).

With the construction thus described, the heating coils 24, 26 can be individually heated by coupling 28 being secured to either of plugs 50, 60. With the use of either direct current or alternating current, the resistive element 22 heats in response to the electrical energy. The heat of the resisting element heats the phase change material 20 such that the phase change material 20 will undergo a phase change.

When heating is complete, the cords 50, 60 may be removed and the pad 10 will retain its energy for a substantial period of time of about two to three hours. As a result, the pad can be heated through either direct current or alternating current. It may be heated in a user's home or in a user's car or place of business. In addition to the foregoing, the vinyl plastic 18 is a microwave transparent material as is cloth 12. The particular phase change material 20 thus described is microwave receptive. Accordingly, the entire pad 10 may be placed in a conventional consumer microwave oven and the necessary energy to heat the phase change material may be applied through microwave energy. For microwave applications, the user may open opening 16A by separating fasteners 40, 41 and folding the coupling 28 into the interior of the cloth covering 12. This prevents the coupling 28 and its metallic elements from being directly exposed to the interior of a microwave oven.

With the foregoing specification, it has been shown how a thermal heating device has been attained in a preferred embodiment of a heating pad. The device may be heated through either microwave energy, alternating current through a standard wall outlet or direct current through an automobile cigarette lighter. While the foregoing description has been made with reference to a preferred embodiment of a heating pad, it will be appreciated that a thermal heating device according to the present invention can be provided in a wide variety of uses and applications such as clothing (footwear, mittens or the like), beverage or food containers or warmers or other devices which are desired to be heated and retain heat for a substantial period of time. Accordingly, it is intended that the scope of the claims of the present invention not be limited by the preferred embodiment but shall include such modifications and equivalents as shall occur to one of ordinary skill in the art having the benefit of the teachings of the present invention.

What is claimed is:

1. A thermal heating and heat storage device comprising:
   (a) a warmer comprising:
      (i) a plastic member defining an interior volume;
      (ii) a phase change material for storage of latent heat positioned within the interior volume of said plastic member;
      (iii) an electrically resistive heating element positioned in thermally conductive contact with said substance;
         (A) said heating element being selectively controllable, upon direction of electric current therethrough, to heat said phase change material to a temperature sufficient for storage of latent heat therein;
         (B) said heating element being positioned within the interior volume of said plastic member;
      (iv) a thermal switch arrangement constructed and arranged to control heating of said electrically resistive heating element;
      (v) an electric power cord having a first end with a coupling; said first end and coupling being positioned exterior to the interior volume of said plastic member; said coupling being a standard electric outlet plug; said electric power cord being in electrically conductive communication with said electrically resistive heating element; and
   (b) an outer covering defining an internal volume receiving and surrounding said warmer, said covering having at least one openable and closeable end;
      (i) said covering and said at least one openable and closeable end being sized for receipt therein of said warmer;

(ii) said at least one openable and closeable end constructed and arranged for selective closure of said at least one openable and closeable end; and (iii) said covering is configured for storage of food, to be maintained warm, therein.

2. A device according to claim 1 wherein:

(a) said outer covering is cloth.

3. A device according to claim 1 wherein:

(a) said outer covering includes a hook-and-loop fastener.

4. A device according to claim 3 wherein:

(a) said thermal switch arrangement is constructed and arranged to prevent heating of said warmer to a temperature above 150° F.

5. A device according to claim 4 wherein:

(a) said thermal switch arrangement is constructed and arranged to control heating of said phase change material to a temperature no higher than 10° F. above a temperature at which said substance begins to convert from a solid to a liquid.

6. A device according to claim 1 including:

(a) open cell foam positioned within the interior volume of said plastic member, along with said phase change material.

7. A device according to claim 1 wherein:

(a) said plastic member is flexible.

8. A device according to claim 1 wherein:

(a) said plastic member is vinyl.

9. A device according to claim 1 wherein:

(a) said standard outlet plug is a 120 watt AC plug.

10. A device according to claim 1 wherein:

(a) said standard outlet plug is a 12 volt DC plug.

11. A thermal heating and heat storage device comprising:

(a) a warmer comprising:

(i) a plastic member defining an interior volume;

(ii) a hydrocarbon containing phase change material for storage of latent heat positioned within the interior volume of said plastic member;

(iii) an electrically resistive heating element positioned in thermally conductive contact with said substance;

(A) said heating element being selectively controllable, upon direction of electric current therethrough, to heat said hydrocarbon containing phase change material to a temperature sufficient for storage of latent heat therein;

(B) said heating element being positioned within the interior volume of said plastic member;

(iv) a thermal switch arrangement constructed and arranged to control heating of said electrically resistive heating element; and (b) an outer covering defining an internal volume having at least one openable and closeable end, said covering receiving and surrounding said warmer;

(i) said covering and said at least one openable and closeable end being sized for receipt therein of said warmer;

(ii) said at least one openable and closeable end constructed and arranged for selective closure of said at least one openable and closeable end; and (iii) said covering is configured for storage of food, to be maintained warm, therein.

12. A thermal heating and heat storage device comprising:

(a) a warmer comprising:

(i) a plastic member defining an interior volume;

(ii) a phase change material for storage of latent heat positioned within the interior volume of said plastic member, said phase change material provided with a phase change temperature of about 140° F.;

(iii) an electrically resistive heating element positioned in thermally conductive contact with said substance;

(A) said heating element being selectively controllable, upon direction of electric current therethrough, to heat said phase change material to a temperature sufficient for storage of latent heat therein;

(B) said heating element being positioned within the interior volume of said plastic member;

(iv) a thermal switch arrangement constructed and arranged to control heating of said electrically resistive heating element;

(v) an electric power cord having a first end with a coupling; said first end and coupling being positioned exterior to the interior volume of said plastic member; said coupling being a standard electric outlet plug; said electric power cord being in electrically conductive communication with said electrically resistive heating element; and (b) an outer covering defining an internal volume having at least one openable and closeable end, said covering receiving and surrounding said warmer;

(i) said covering and said at least one openable and closeable end being sized for receipt therein of said warmer;

(ii) said at least one openable and closeable end constructed and arranged for selective closure of said at least one openable and closeable end; and (iii) said covering is configured for storage of food, to be maintained warm, therein.

\* \* \* \* \*